(12) United States Patent
Pinter

(10) Patent No.: US 6,277,142 B1
(45) Date of Patent: Aug. 21, 2001

(54) METHOD AND APPARATUS FOR PROMOTING ENERGY FLOW IN AN ORGANISM

(75) Inventor: Joze Pinter, Pennington, NJ (US)

(73) Assignee: Biomega, Inc., Pennington, NJ (US)

( * ) Notice: Subject to any disclaimer, the term of this patent is extended or adjusted under 35 U.S.C. 154(b) by 0 days.

(21) Appl. No.: 09/173,670

(22) Filed: Oct. 16, 1998

Related U.S. Application Data

(63) Continuation-in-part of application No. 09/086,957, filed on May 29, 1998, now abandoned.

(51) Int. Cl.$^7$ .................................................. A61N 1/00
(52) U.S. Cl. .............................................................. 607/1
(58) Field of Search ................................ 600/9; 606/204; 607/1, 2, 144

(56) References Cited

U.S. PATENT DOCUMENTS

| | | | | |
|---|---|---|---|---|
| 881,840 | * | 3/1908 | Askins | 607/144 |
| 2,904,724 | * | 9/1959 | Mendoze | 607/144 |
| 3,987,787 | * | 10/1976 | Booxer | 606/204 |
| 4,033,054 | | 7/1977 | Fukuoka . | |
| 4,411,258 | * | 10/1983 | Pujals, Jr. | 606/204 |
| 4,632,095 | | 12/1986 | Libin . | |
| 4,694,831 | | 9/1987 | Seltzer . | |
| 4,808,469 | | 2/1989 | Hiles . | |
| 4,841,647 | | 6/1989 | Turucz . | |
| 5,070,862 | | 12/1991 | Berlant . | |
| 5,158,526 | * | 10/1992 | Bricot | 600/9 |
| 5,199,876 | | 4/1993 | Waldman . | |
| 5,448,777 | * | 9/1995 | Lew | 606/204 |

FOREIGN PATENT DOCUMENTS

0024124 * 11/1899 (GB) .................................. 607/144

OTHER PUBLICATIONS

Maggie La Tourelle and Anthea Courtenay, Thorsons Introductory Guide to Kinesiology, Harper Collins Publisher, pp 14–23,51–52, (1992).

Mildred Carter and Tammy Weber, "Healing Yourself with Foot Reflexology", Prentice–Hall Inc., pp 3–6, (1977).

Mildred Carter and Tammy Weber, "Body Reflexology", Parker Publishing Co., pp 3–5, (Rev. 1994).

Kevin and Barbara Kunz, "Hand and Foot Reflexology A Self–Help Guide", Prentice–Hall Inc., pp 2–5, 11–12, (1987).

Richard Gherber, "Vibrational Medicine—New Choices for Healing Ourselves", Bear & Company, pp 203–215, (1966).

\* cited by examiner

*Primary Examiner*—William E. Kamm
(74) *Attorney, Agent, or Firm*—Andrew F. Reish

(57) ABSTRACT

An apparatus for promoting energy flow in an organism includes a plurality of conductive elements and a dielectric material. The conductive elements are disposed on the dielectric material in a predetermined spatial relationship. The apparatus further includes an overlaying mechanism which supports the dielectric material with the conductive elements across predetermined regions of the organism. The predetermined regions include reflex points where the first conductive element of the conductive elements channelizes energy from a first reflex point in the vicinity of a first meridian in the organism. The first conductive element transmits the energy received from the first reflex point to a second conductive element of the conductive elements. The second conductive element transmits the received energy to a second reflex point in the vicinity of at least one of the first meridian and a second meridian in the organism, whereby healthy flow of energy throughout the organism energy is substantially increased.

40 Claims, 7 Drawing Sheets

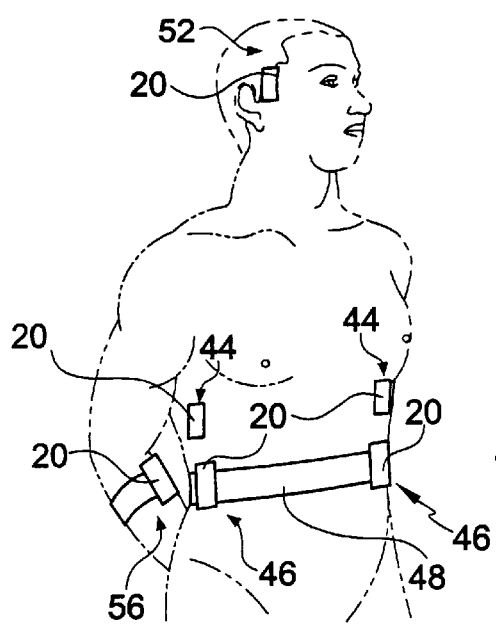
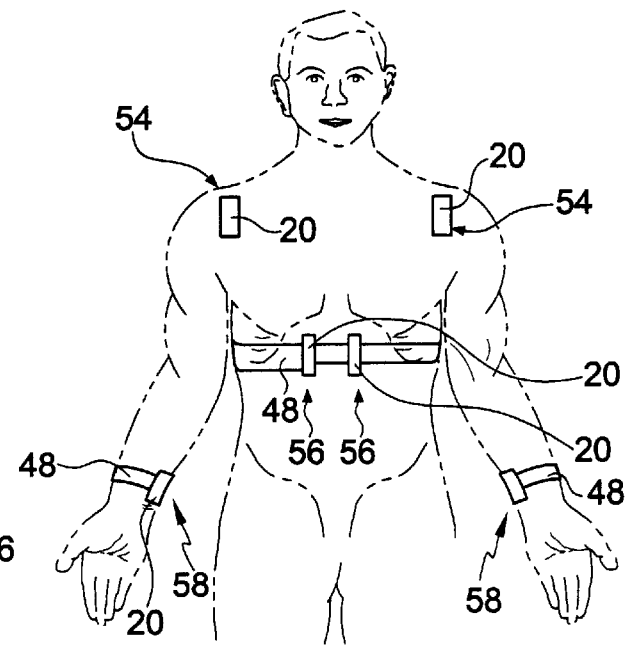
FIG.2  FIG.3
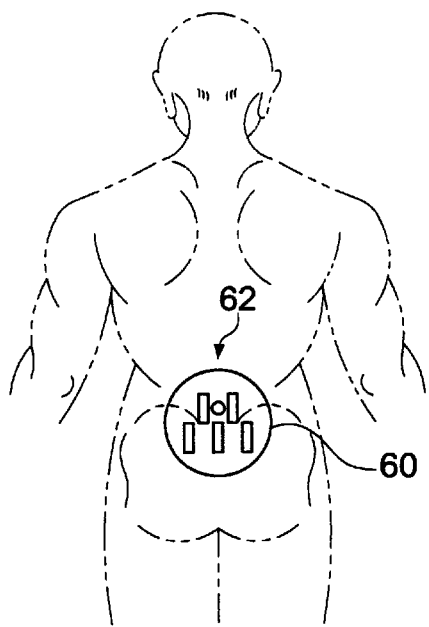
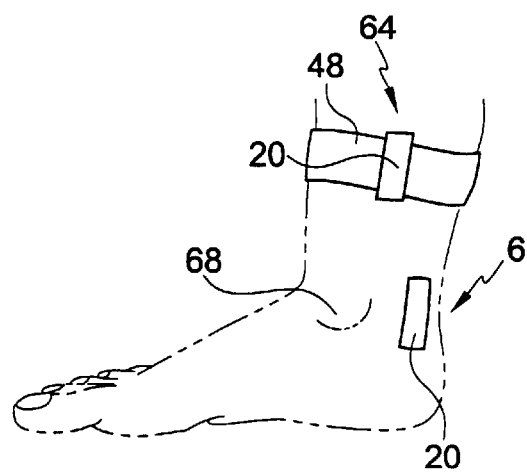
FIG.4  FIG.5

FIG.10
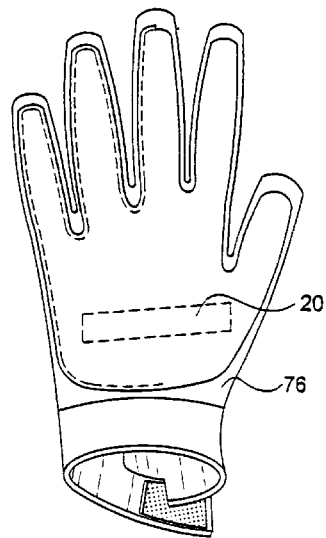
FIG.11
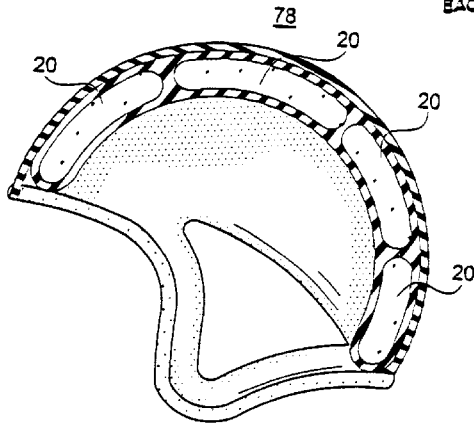
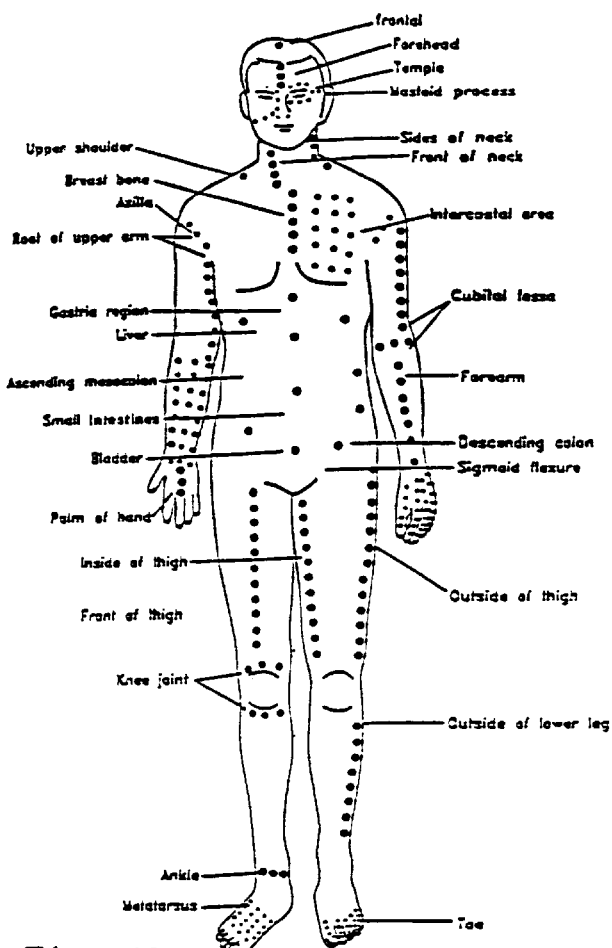
Fig. 12
BACKGROUND ART

METHOD AND APPARATUS FOR PROMOTING ENERGY FLOW IN AN ORGANISM

This application is a continuation-in-part of application Ser. No. 09/086,957, filed May 29, 1998 (now abandoned).

BACKGROUND OF THE INVENTION

1. Field of the Invention

The present invention relates to a method and apparatus for promoting healthy flow of energy throughout an organism. The method and apparatus employ conductive elements which are placed adjacent to the organism. The conductive elements overlay singular or multiple energy pathways called meridians, each relating to specific organs, glands or systems of the organism.

2. Description of the Background Art

Various forms of natural medicine exist today. Two forms of natural medicine which have received much attention from the conventional modern scientific medical community as well as the natural medicine communities are kinesiology and reflexology. Both of these forms of natural medicine focus on energy flow throughout an organism. This energy flow is often referred to as "subtle energy" which is drawn to systems of energy within and around the body.

Subtle energy is similar or analogous to Qi (pronounced chi) of Chinese acupuncture and other natural healing techniques which focus on a universal life-force that is vital to the health of the mind and body of an organism. Many texts have been published on, or discuss, the subjects of reflexology and kinesiology. Such texts include at least the following: Maggie La Tourelle and Anthea Courtenay, *Thorsons Introductory Guide to Kinesiology*, Harper Collins Publisher (1992); Mildred Carter and Tammy Weber, *Healing Yourself with Foot Reflexology*, Prentice-Hall Inc. (1997); Mildred Carter and Tammy Weber, *Body Reflexology*, Parker Publishing Co. (Rev. 1994); Kevin and Barbara Kunz, *Hand and Foot Reflexology A Self-Help Guide*, Prentice-Hall Inc. (1987); and Richard Gherber, *Vibrational Medicine*—New Choices for Healing Ourselves, Bear & Company (1996).

The La Tourelle publication states that the terms "energy medicine" and "vibrational medicine" are being increasingly applied by doctors as well as natural therapists to a whole group of natural healing systems, which include acupuncture and kinesiology. The La Tourelle publication further states that subtle energy has always been seen and felt by healers and acupuncturists who are trained to read the flow of Qi through twelve specific pulses on the limb of a human body (a wrist). The pulse locations are connected with a series of energy pathways called meridians, each meridian relating to a specific organ, gland, or system of the organism. See La Tourelle publication, pages 14–15.

The La Tourelle publication explains that in kinesiology a further connection has been made between meridians and specific muscles, with which the muscles are "energetically" connected. Kinesiology uses manual muscle testing to assess the organism's energy and then applies a range of techniques to promote the healthy flow of energy throughout the organism. The La Tourelle publication explains that the ancient philosophy of Chinese medicine states that health comes from being in balance and in harmony with all things, where balance is a perfect state in which no aspect is either deficient or in excess. See La Tourelle publication, page 15.

Kinesiologists use muscle testing to discover energy imbalances (deficient or excess energy) which can affect an organism's health. Kinesiologists draw on theories of acupuncture to understand how these energies can be balanced. The La Tourelle publication further defines reflex points as points on or near the surface of the organism which are connected with parts of the organism not necessarily found in the same area. Stimulating reflex points, for example, by gently rubbing them, has an affect on the part of the organism which is not necessarily found in the same area of the rubbing. The La Tourelle publication explains that kinesiology correction techniques include holding or gently massaging a number of the reflect points.

The La Tourelle publication explains that energy circuits exist in organisms such as the human body and that energy fields extend to within two inches/five centimeters around the body. The La Tourelle publication further explains the electromagnetic problems within an organism such as a human body are caused by electrical disturbances in these energy circuits which create poor or faulty communication with the body, often giving rise to feelings or disorientation and confusion, poor coordination, dyslexia, etc. The La Tourelle publication further provides that electromagnetic factors include at least the following: ionization which involves the balance of positive and negative ions that can be breathed in by an organism which create positive and negative currents within the organism; acupuncture meridians (energy pathways) which involve fourteen meridians for over- and under-energy, each relating to a specific part or parts of the body; and right/left brain hemisphere integration.

The Carter Publication drawn to body reflexology defines reflex points as energy junctions that relay and reinforce energy along meridian lines of an organism, passing energy towards organs in the nervous system. The same Carter publication explains that experiments and testing with electrodes have provided scientific proof that electrical current passes most readily along an organism's meridian lines. The Carter publication further explains that, in view of this testing, it has now been determined that specific electrical properties exist at the reflex points and around the meridians that are different from the surrounding tissues. See page 4 of the publication.

The Carter publication drawn to foot reflexology explains that reflexology is a scientific technique of applying pressure to reflexes that have a definite affect on the normal functioning of all parts of an organism such as the human body. The same publication provides that when properly performed, a reflex massage sends stimuli to various organs, glands, and nerves in the body. The Carter publication states that tenderness at particular points, which are most commonly found in the limbs of an organism such as in the feet and the hands of the human body, may indicate congestion of energy within the organism or body. The Carter publication states that the purpose of reflexology is to promote balance and normalization, to reduce tension, to revitalize, reactivate, regenerate, heal, and bring the whole system of an organism into harmony in a state of good health, naturally. The Carter publication drawn to foot reflexology further provides that the application of pressure to reflex points promotes vital energy that runs vertically through the body (the right foot of a human body corresponds to the right side of the human body, while the left foot corresponds to the left side of the human body). See page 3 of such publication.

The Gherber publication explains the presence of multi-dimensional energy fields in a living organism. These fields include subtle energy fields and electromagnetic energy fields. This publication further explains the need to balance these fields to promote good health. It particularly notes the benefits arising from the use of electromagnetic fields as a promoter of healing in bone fracture therapy.

U.S. Pat. No. 4,632,095 to Libin explains how various organs, nerves, and glands in a living organism such as the human body are connected with certain "reflex areas" on the bottoms of feet, hands, and other areas of the human body. The Libin patent explains how reflexology involves massaging these corresponding reflex areas and through resulting stimulatory responses, prompt help or the promotion of energy flow for conditions of the body can often be obtained. FIG. 12 of the present specification, which is derived from the Libin patent, provides a typical chart showing some of the pressure points in an organism such as the human body.

U.S. Pat. No. 5,199,876 to Waldman provides teachings of hand reflexology which is the process of directly stimulating the reflex points in the limb of an organism such as the hand of a human body, the reflex points directly correspond to an organism's internal organs and functions. The Waldman patent explains how an organism such as the human body is divided into ten areas of jurisdiction (meridians), where each area contains its corresponding organs with a reflex counterpart in the hand. An organism such as a human body is shown in FIG. 14 of the present specification, the figure being derived from the Waldman patent. FIG. 14 illustrates the contiguous reflex area lines called meridians contained within a human body. FIGS. 15A and 15B of the present specification, which are also derived from the Waldman patent, provide morphological area maps which identify naturally occurring organ reflex receptor area points or areas in a hand of a human body. FIGS. 15A and 15B further provide approximate locations of the reflex area lines or meridians labeled 1, 2, 3, 4, and 5 which correspond to the reflex area lines or meridians shown in FIG. 14 of the present specification.

U.S. Pat. No. 4,841,647 to Turucz relates to insoles for shoes and more particularly to insoles having foot massaging projections extending from the upper surface of the insoles which massage feet of an organism during walking. The Turucz patent states that application of rhythmic pressure to reflex areas affect the well-being of organs in organisms such as the human body which are connected by either nerves or energy channels which terminate at these reflex areas. FIG. 13 of the present specification which is derived from the Turucz patent shows an example of reflex areas which are present on feet of the human body. The Turucz patent provides projections having configurations that are superimposed below the reflex areas of a human foot in the shoes of a person wearing the shoes. The Turucz patent explains that the action of walking creates a rhythmic pressure on the soles of the feet at locations or areas of the shoes overlying the projections and thereby stimulates a deep massaging at the reflex areas.

U.S. Pat. No. 4,694,831 to Seltzer explains that reflex points on the feet of a human body are designed so as to positively affect the lower terminus of internal-lines commonly called meridians which regulate the normal flow of energy throughout the organism such as the human body. The Seltzer patent states that in accordance with oriental medical theory such as Chinese acupuncture/acupressure, each meridian is linked with one of the major organs of the organism such as the human body, and which includes the heart, lungs, liver, stomach, eyes, ears and reproductive organs.

The Seltzer patent provides that energy circulates through the meridians starting with the lungs of the human body which draw oxygen into the organism or human body every twenty-four hours. The Seltzer patent explains that when energy is blocked, an excess of energy develops in that organ. Conversely, if the energy flow circulates too freely, the organs will suffer from deficiency. As a result, in either case, illness, pain, and body dysfunction may occur. The Seltzer patent then concludes that acupressure application by footwear with projections is capable of effectively massaging the soles of the feet which in turn stimulates appropriate meridians and brings the so-called life-force energy back into healthful balance. The massaging of the reflex points also helps enhance or normalize circulation through the organism or body. The Seltzer patent further provides that acupressure works to maintain continuous good health and to aid normal body functioning.

Each of the aforementioned patents and printed publications do not provide any teachings of a method or apparatus which employs at least one of conducting energy from an organism and retransmitting the energy back to the organism and a combination of massaging the reflex points or termini on, or in the vicinity of, meridians and receiving and retransmitting energy from the organism. The aforementioned patents and printed publication are primarily concerned with massage techniques which require physical and taxing mechanical manipulation of parts of an organism.

Various massage devices exist in the background art which provide therapeutic electro-massage which involves delivery of electrical energy to an organism through the surface of the organism to excite underlying nerves. For example, U.S. Pat. No. 5,070,862 to Berlant provides an electrode glove for use by a therapist to effectively apply a combination of whole hand massage and electrical stimulation to a patient. However, similar to the aforementioned patents and printed publications drawn to the mechanical manipulation of reflex points, the Berlant patent also requires manual massage techniques in addition to active stimulation of an organism from an electrical sources outside the organism such as Direct or Alternating current from either a respective battery or AC power source.

U.S. Pat. No. 4,033,054 to Fukuoka provides a teaching of stimulating reflex points on the foot of the human body with multiple projections which include magnets that project magnetic fields upon the foot of the human body. The Fukuoka patent explains that magnetic stimulation of reflex points on a foot of an organism improves blood circulation, supplies the foot with blood and makes a foot warmer. The Fukuoka patent provides that the effectiveness of the magnetic stimulation depends upon the manner and degree of close contact of the magnet with the sole of the foot. The Fukuoka patent employs magnets as massaging projections as well as active elements which project magnetic fields into the human body.

The aforementioned background art requires either mechanical stimulation of the parts of an organism or a combination of mechanical stimulation with active elements such as magnets or electrical sources external to an organism. Much of the background art requires specific massaging techniques that are often cumbersome in addition to requiring the organism to reduce the level of physical activity to focus on the massaging techniques. While a few of the patents, such as the Seltzer, Turucz and Fukuoka patents provide massaging devices which include predetermined projections contacting a foot of an organism such as the human body, these patents are designed to actively massage or interact with the organism or human body that is readily perceptible by the organism.

Such massaging techniques can distract the organism or cause mild discomfort due to the active mechanical stimulation which is either new or foreign to the organism. Additionally, only the Fukuoka patent provides a combination of an active magnetic element with massaging techniques which are applied to a foot or an organism. While the Fukuoka patent employs magnetic fields to the organism or human body, these magnetic fields are generated externally of the organism and must be applied in combination with massaging techniques which are readily perceptible to the organism as noted above.

Accordingly, a need exists in the art for a method and apparatus which promotes energy flow in an organism without requiring the organism to stop activity to focus on massaging techniques or requiring the organism to wear massaging devices which are substantially designed to project at predetermined points into the body of the organism to facilitate massaging techniques. A further need exists in the art to provide a method and apparatus for promoting energy flow in an organism which does not require projecting members which press into or upon an organism in combination with purely active elements that only emit energy such as magnetic or electromagnetic fields.

SUMMARY OF THE INVENTION

Accordingly, it is a primary object of the present invention to provide a method and apparatus for promoting energy flow in an organism which does not require extensive mechanical manipulation of reflex points or meridian termini of an organism.

It is a further object of the present invention to provide a method and apparatus, a bioenergy channelizer unit, for promoting healthy energy flow in an organism which can be worn on, at or in the vicinity of various portions of an organism to receive and transmit energy to and from the organism.

Another object of the present invention is to provide a method and apparatus which is worn on the organism on, at, or in the vicinity of, reflex points or meridian termini in order to promote healthy energy flow through specific organs, glands, or systems within the organism.

It is a further object of the present invention to provide a method and apparatus that promotes healthy energy flow with the organism having a reduced perception of the presence of the bioenergy channelizer unit.

It is a further object of the present invention to provide a method and apparatus which promotes healthy energy flow about an organism by substantially reducing energy imbalances (deficient or excess energy) which occur between reflex points along or in the vicinity of the meridians in an organism.

Another object of the present invention is to promote healthy flow of energy along or in the vicinity of energy channels or meridians in the organism and the balancing of energy along meridians and/or across meridians or in the vicinity of meridians which is dependent upon the location of the bioenergy channelizer unit.

These and other objects of the present invention are fulfilled by providing a method for promoting energy flow in an organism comprising the steps of: providing a plurality of conductive elements; placing the conductive elements on a dielectric material in a predetermined spatial relationship; overlaying the dielectric material with the conductive elements across predetermined regions of the organism; channelizing energy with the conductive elements from a first reflex point or area in the vicinity of a first meridian of the organism; transmitting energy with the conductive elements received from the first reflex point to a second reflex point in the vicinity of at least one of the first meridian and a second meridian of the organism, whereby health flow of energy within the organism is substantially increased.

In addition, these and other objects of the present invention are also accomplished by providing an apparatus for promoting energy flow in an organism comprising: a plurality of conductive elements; a dielectric material, the conductive elements are disposed on a dielectric material in a predetermined spatial relationship; means for overlaying the dielectric material with the conductive elements across predetermined regions or portions of the organism, the predetermined regions including reflex points or areas, a first conductive element of the conductive elements channelizes energy received from a first reflex point in the vicinity of a first meridian of the organism, the first conductive element transmits the energy received from the first reflex point to another conductive element of the conductive elements, the another conductive element transmits the received energy to a second reflex point in the vicinity of at least one of, the first meridian and a second meridian in the organism, whereby healthy flow of energy within the organism is substantially increased.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 2 illustrates several locations for the application of the bioenergy channelizer unit on an organism such as the human body;

FIG. 3 shows additional preferred locations of the application of the bioenergy channelizer unit on an organism such as the human body;

FIG. 4 shows additional preferred locations of the bioenergy channelizer unit applications on an organism such as the human body;

FIG. 5 shows further preferred locations of the application of the bioenergy channelizer unit on an organism such as the human body;

FIG. 10 shows another embodiment of the present invention where the bioenergy channelizer unit is applied to an article of apparel such as gloves;

FIG. 11 shows a further embodiment of the present invention where the bioenergy channelizer unit is applied to an article of apparel such as a helmet;

FIG. 12 provides background art of various reflex points on an organism such as the human body;

DETAILED DESCRIPTION OF THE PREFERRED EMBODIMENTS

Figure 1A:
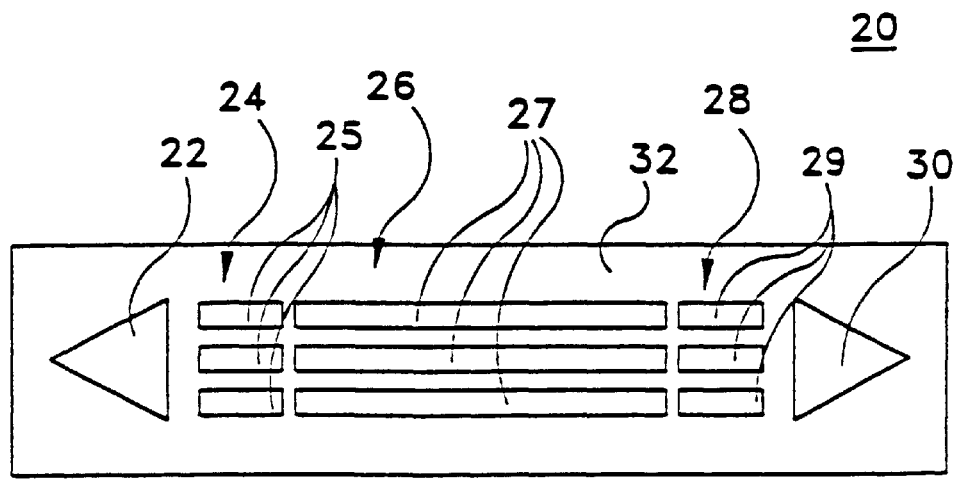
FIG. 1A is an elevational view of the bioenergy channelizer unit of the present invention.

Referring in detail to the drawings and with particular reference to FIG. 1A, and apparatus for promoting energy flow or a bioenergy channelizer unit 20 is shown. The bioenergy channelizer unit promotes energy flow in an organism by receiving energy from the organism and retransmitting this received energy back to the organism. (However, additionally, it is noted that movement of a unit through an electrical, magnetic, electromagnetic or other energy field may cause energy flow along the unit.) The bioenergy channelizer unit is preferably used on an organism such as the human body, but other organisms such as animals, plants or other living organisms are not beyond the scope of the present invention. The bioenergy channelizer unit 20 relates to energy which propagates through an organism which is synonymous with Qi (pronounced chi) of Chinese acupuncture, and with Prana of traditional Indian medicine and philosophy, and energy associated with the universal life-force present in an organism. The energy discussed herein also relates to the energy which is associated with kinesiology and reflexology.

The bioenergy channelizer unit 20 "channelizes" or "harnesses" energy emitted from an organism which can take many forms. Such forms of energy emitted from the human body include, but are not limited to, electromagnetic energy, magnetic energy in the form of magnetic fields, biochemical energy, and thermal energy or other like energy forms.

The bioenergy channelizer unit is preferably designed to receive energy that flows within the meridians or energy channels of a living organism. It is contemplated that the bioenergy channelizer unit receives energy from one reflex point in the vicinity of one meridian and transmits energy to another reflex point in the vicinity of that or another meridian. However, the bioenergy channelizer unit 20 can receive energy from along a single meridian and retransmit energy to the same meridian from which the energy was received. The bioenergy channelizer unit 20 can receive energy from at least one reflex point with respect to at least one meridian and transmit this received energy to one or more reflex points at one or more meridians. Alternatively, the bioenergy channelizer unit 20 can receive energy from the vicinity of one meridian and retransmit the received energy to the vicinity of a plurality of meridians within a living organism.

The bioenergy channelizer unit 20 preferably includes a plurality of conductive elements 22, 24, 26, 28, and 30. The conductive elements 22, 24, 26, 28, and 30 are preferably made from silver but other conductive materials forming one or more of the elements are not beyond the scope of the present invention. Other materials include but are not limited to other precious metals such as gold, but include copper, stainless steel, various alloys, nonferrous alloys, nonferrous materials, ceramic materials and other conductive materials which promote energy flow within an organism. It is contemplated that when energy is emitted from an organism in the form of a magnetic field, at least one of the conductive elements 22, 24, 26, 28, and 30 will move relative to the lines of force of such a magnetic field to promote or induce an electric current therein. However, as stated above, the energy forms propagating through an organism can include, but are not limited to, electromagnetic energy, magnetic energy, electrical energy, chemical energy, thermal energy, and other like energy forms.

In the preferred embodiment of the invention as shown in FIG. 1A, the bioenergy channelizer unit 20 includes a first conductive element 22 which has a predetermined geometrical shape. In the preferred embodiment, the preferred geometrical shape of the first conductive element 22 is a triangle. However, other shapes of the first conductive element are not beyond the scope of the present invention. Other shapes include but are not limited to circular, elliptical, square, rectangular, pentagonal, hexagonal, octagonal, and other polygonal shapes. While only a single conductive element 22 is shown in FIG. 1A, a plurality of conductive portions which are grouped in the shape of a triangle is not beyond the scope of the present invention. In other words, a plurality of conductive sub-parts which form a triangular perimeter could also be employed as the first conductive element 22. As to dimensions of the preferred triangular shaped embodiment of the first conductive element 22, through study and experimentation, the inventor has determined that the ratio of the distance from the distal point of the structure to the base width of the structure is less than 1, preferably in a ratio of 7/10, and more preferably 11/15.

A second conductive element 24 preferably includes a plurality of conductive portions 25. Each of these second conductive portions 25 preferably has a rectangular shape however, similar to the first element 22, other shapes are not beyond the scope of the present invention. Other shapes include but are not limited to elliptical, circular, square, trapezoidal, pentagonal, hexagonal, octagonal and other like polygonal forms. Each of the second conductive portions 25 includes a surface area which is equivalent with respect to a neighboring conductive portion 25 of the plurality. While portions 25 of the second conductive element 24 are shown, it is not beyond the scope of the present invention to form the second conductive element 24 as a single conductive portion.

The conductive portions 25 are preferably aligned in a parallel manner adjacent to the first conductive element 22. The second conductive portions 25 preferably include first sides and second sides where the first sides are substantially larger than the second sides. The second smaller sides are preferably aligned in a parallel manner with respect to one side of the first conductive element 22 which is typically triangularly shaped. The second conductive portions 25 are spaced from the conductive element 22 according to a predetermined distance which facilitates energy flow between conductive elements and a living organism.

The third conductive element 26 includes a plurality of conductive portions 27 which are spaced apart from the second conductive portions 25 by a predetermined distance which facilitates energy flow between the conductive elements/portions and a living organism. Similar to the second conductive portions 25, the third conductive portions 27 preferably include a rectangular shape. However, each third conductive portion 27 preferably includes surface areas which are substantially larger than the surface areas of the second conductive portions 25. While the conductive portions 27 are preferably rectangular in shape, other shapes of the third conductive portions 27 include but are not limited to circular, elliptical, square, pentagonal, hexagonal, octagonal and other polygonal shapes.

The third conductive portions 27 are preferably substantially aligned in a parallel manner and include first sides and second sides. Each first side of each third rectangular conductive portion 27 is substantially larger than each second side of each third conductive portion 27. The second sides of the third conductive portions 27 are substantially aligned in a parallel manner with respect to the second sides of the second conductive portions 25.

The third conductive portions 27 are spaced apart from each other for a predetermined distance and are spaced apart from the second conductive portions 25 by a predetermined distance which substantially promotes energy flow between the conductive elements in addition to energy flow between the conductive elements and the organism. Similar to the second conductive portions 25, the third conductive portions 27 can include a single conductive portion formed in a unitary structure or can include additional conductive portions which form a substantially similar shape of the plurality of third conductive portions 27 shown in FIG. 1A. In other words, a single conductive portion can replace the three conductive portions 27 shown in FIG. 1A or the third conductive element 26 can include 4, 5, or 6 separate portions or multiples of three conductive elements such as 6, 9, and 12, instead of the three conductive portions 27 shown.

The fourth conductive element 28 includes a plurality of conductive portions 29 which are substantially similar to the second conductive portions 25. Therefore, since the third conductive portions 29 are substantially similar to the second conductive portions 25, a description of the fourth conductive portions 29 is not necessary.

Similar to the fourth conductive portions 29 relative to the second conductive portions, the fifth conductive element 30 is substantially similar in structure to the first conductive element 22. The fifth conductive element 30 can include alternate embodiments similar to those discussed with reference to the first conductive element 22 where multiple portions form the fifth conductive element 30. Additionally, the previously noted ratio dimensions of the first conductive element 22 are applicable to the fifth conductive element. Accordingly, further discussion of the fifth conductive element 30 is not necessary.

Viewing the bioenergy channelizer unit as a whole, the symmetry of the whole unit 20 is apparent to an observer. The first triangular conductive element 22 "points" or is directed in a first direction while the fifth triangular conductive element 30 "points" or is oriented in a second direction which is substantially 180° relative to the first direction of the first conductive element 22. The symmetry of the bioenergy channelizer unit 20 is further emphasized by the second conductive element 24 which is disposed between the first conductive element 22 and the second conductive 26 while the fourth conductive element 28 is disposed between the third conductive element 26 and the fifth conductive element 30. It is believed that the relative spacing between the elements (within a specified group such as the spacing between respective portions 25) in addition to the relative spacing between adjacent conducting elements (such as elements 24 and 26) and the spacing of the conductive elements 22, 24, 26, 28, and 30 with respect to an organism promote energy flow from the living organism to the conductive elements 22, 24, 26, 28, and 30 and back to the living organism. The conductive elements 22, 24, 26, 28, and 30 are preferably disposed upon a dielectric layer 32.

FIG. 1A shows the bioenergy channelizer unit 20 without first or second covering layers 34 and 42 or dielectric layers 32 and 40. The first covering layer 34 is preferably a dielectric material. The dielectric material is preferably leather, Gore-Tex™, Altacara, or Silon (preferably with microcapsules of etheric oils contained within its structure), but other types of dielectric materials are not beyond the scope of the present invention. Other types of materials include but are not limited to silicon, polyethylene, Teflon™, polystyrene, polyvinyl chloride, nylon, rubber epoxy, paraffin wax, fused silica and water and other like dielectric materials.

Figure 1B:
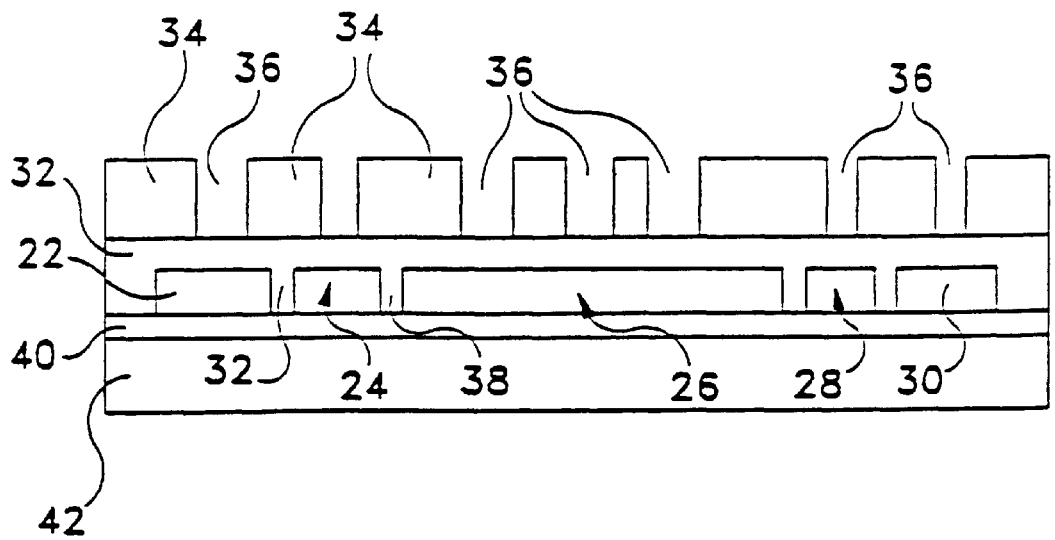
FIG. 1B is a cross-sectional view of the bioenergy channelizer unit of the present invention.

As seen in FIG. 1B which shows a complete cross section of the bioenergy channelizer unit 20 along with the covering layer 34 which includes a plurality of apertures 36 which penetrate completely through the first covering layer 34 to expose surfaces of the first dielectric material layer 32. The apertures 36 are preferably circular in shape, but other shapes are not beyond the scope of the present invention. Other shapes of the apertures 36 include but are not limited to elliptical, square, rectangular, pentagonal, hexagonal, octagonal and other like polygonal shapes. The apertures preferably have a maximum diameter of 1 mm. However, other sizes are not beyond the scope of the present invention. However, dependent on the use of materials for first covering layer 34 and/or anticipated siting of the bioenergy channelizer unit 20 on the organism, the apertures 36 are optional such that the first covering layer 34 has no formed apertures which penetrate completely through the layer.

Between the conductive elements 22, 24, 26, 28, and 30, the first dielectric material layer 32 is preferably disposed. However, it is possible to form the bioenergy channelizer unit where an absence of material or lack of material is present between the respective conductive elements 22, 24, 26, 28, and 30. For example, the spaces or pockets 38 can be filled with atmospheric air or a vacuum. The conductive elements 22, 24, 26, 28, and 30, are further disposed upon a second dielectric layer 40 which is preferably silicon. However, other types of dielectric materials are not beyond the present invention and include but are not limited to leather, polyethylene, Teflon™, polystyrene, polyvinyl chloride, nylon, rubber epoxy, paraffin wax, fused silica and water and other like dielectric materials. Furthermore, it is not beyond the scope of the present invention where the first dielectric layer 32 and second dielectric layer 40 are essentially one dielectric layer which encapsulate the conductive elements 22, 24, 26, 28, and 30. Such an embodiment where the dielectric layers 32 and 40 are a unitary structure would facilitate efficient manufacturing of the bioenergy channelizer unit 20.

The thickness of the first dielectric 32 and the second dielectric layer 40 are dependent upon the amount of energy emitted from the living organism in which the bioenergy channelizer unit 20 is attached thereto. Therefore, the thicknesses of the dielectric layers can vary depending upon the strength of the energy being emitted from the living organism. It is contemplated that the spacings between the conductive elements 22, 24, 26, 28, and 30 and the thickness of the dielectric layers 32 and 40 are dependent upon the particular energy field of an organism where each living organism may include different energy field strengths with respect to a similar living organism.

The second dielectric layer 40 may also be spaced between the conductive elements 22, 24, 26, 28, and 30, in addition to the dielectric layer 32, and a second covering layer 42. The second covering layer 42 is preferably made of a dielectric material similar to the material of the first covering layer 34 (leather, Gore-Tex™, or Altacara). While the second covering layer 42 has a thickness which is dependent upon the amount of energy being emitted from the living organism, the thickness of the second covering layer 42 is also dependent upon the intended environment of the bioenergy channelizer unit 20.

For example, when the bioenergy channelizer unit 20 is attached to or incorporated in an article of apparel, such as foot soles or footwear, the thickness of either of the first covering layer 34 or the second covering layer 42 may depend upon other materials that lie adjacent to the second covering material such as the inner soles of shoes. In other embodiments, the thickness of either of the first covering layer 34 or the second covering layer 42 could depend upon the thickness of the article of apparel in which the bioenergy channelizer unit is attached to, such as in the case when the bioenergy channelizer unit 20 is attached to or incorporated in a glove fitting over a limb of an organism. Furthermore, for manufacturing efficiency, one or more bioenergy channelizer units 20 may share in common either a first covering layer 34, second covering layer 42, first dielectric layer 32 or second dielectric layer 40 which is an element of or incorporated in an article of apparel or body covering. An example of such sharing of a common first covering layer 34 or a common second covering layer 42, and optionally the first dielectric layer 34 and second dielectric layer 40, is the use of multiple bioenergy channelizer units in a footsole in which the units are sandwiched or incorporated between an outer sole acting as a second covering layer 42 and an inner sole acting as a first covering layer 34.

The thicknesses and the relative spacings between the conductive elements 22, 24, 26, 28, and 30 with respect to the living organism and the surrounding dielectric layers 32 and 40 and the covering layers 34 and 42 can be varied in accordance with the amount of energy interaction that an organism desires to occur between the bioenergy channelizer unit 20 and the organism.

In FIG. 2, preferred locations of the bioenergy channelizer unit with respect to an organism such as the human body are shown. The bioenergy channelizer unit disposed at location 44 is adjacent reflex points in the vicinity of meridians of the human body which correspond to the spleen organ. The bioenergy channelizer units at locations 44 can be attached to the human body by adhesives which form the first covering layer 34 of the bioenergy channelizer units 20. At locations 46, the bioenergy channelizer units are disposed adjacent to reflex points in the vicinity of meridians which correspond with the human liver organ. The bioenergy channelizer units 20 at locations 46 are attached to the human body or living organism by an overlaying mechanism 48.

The overlaying mechanism 48 can include a fabric material which is expandable. However, other overlaying mechanisms include, but are not limited to, articles of apparel, adhesives, rubber materials, yarns, strings, adhesive tapes, or other like-fastening structures which can attach to a living organism.

In FIG. 2, a bioenergy channelizer unit 20 is also disposed on an arm portion 50 which is adjacent to reflex points in the vicinity of a meridian that corresponds to the large intestine of a human body. A bioenergy channelizer unit 20 is also disposed at locations 52 on the skull of a human body which correspond to the "Sanjiao Meridian."

In FIG. 3, the bioenergy channelizer unit 20 is disposed at locations 54 which correspond to reflex points in the vicinity of meridians associated with the human lungs. Bioenergy channelizer units 20 are also disposed at locations 56 which correspond to reflex points in the vicinity of stomach meridians of the human body. At locations 58, bioenergy channelizer units 20 are disposed and interact with reflex points in the vicinity of meridians which correspond to the heart of a human body. At locations 56 and 58 overlaying mechanisms 48 are employed, however, such overlaying mechanisms 48 are not required when adhesive type mechanisms are employed to attach the bioenergy channelizer unit to the living organism. In FIG. 4, a set 60 of bioenergy channelizer units 20 are shown to be attached at a location 62 which corresponds to the "Du Mai" meridians.

In FIG. 5, an attachment mechanism 48 is employed to overlay a bioenergy channelizer unit 20 at a location 64 which corresponds to reflex points in the vicinity of meridians that are associated with the spleen organ of the human body. The bioenergy channelizer unit 20 is attached to the human body at location 66 which is adjacent to reflex points in the vicinity of a meridian which is associated with the kidney organs of the human body. Reference numeral 68 denotes a location which is often known as the "Medial Malleolus."

Figures 6, 7, 8:
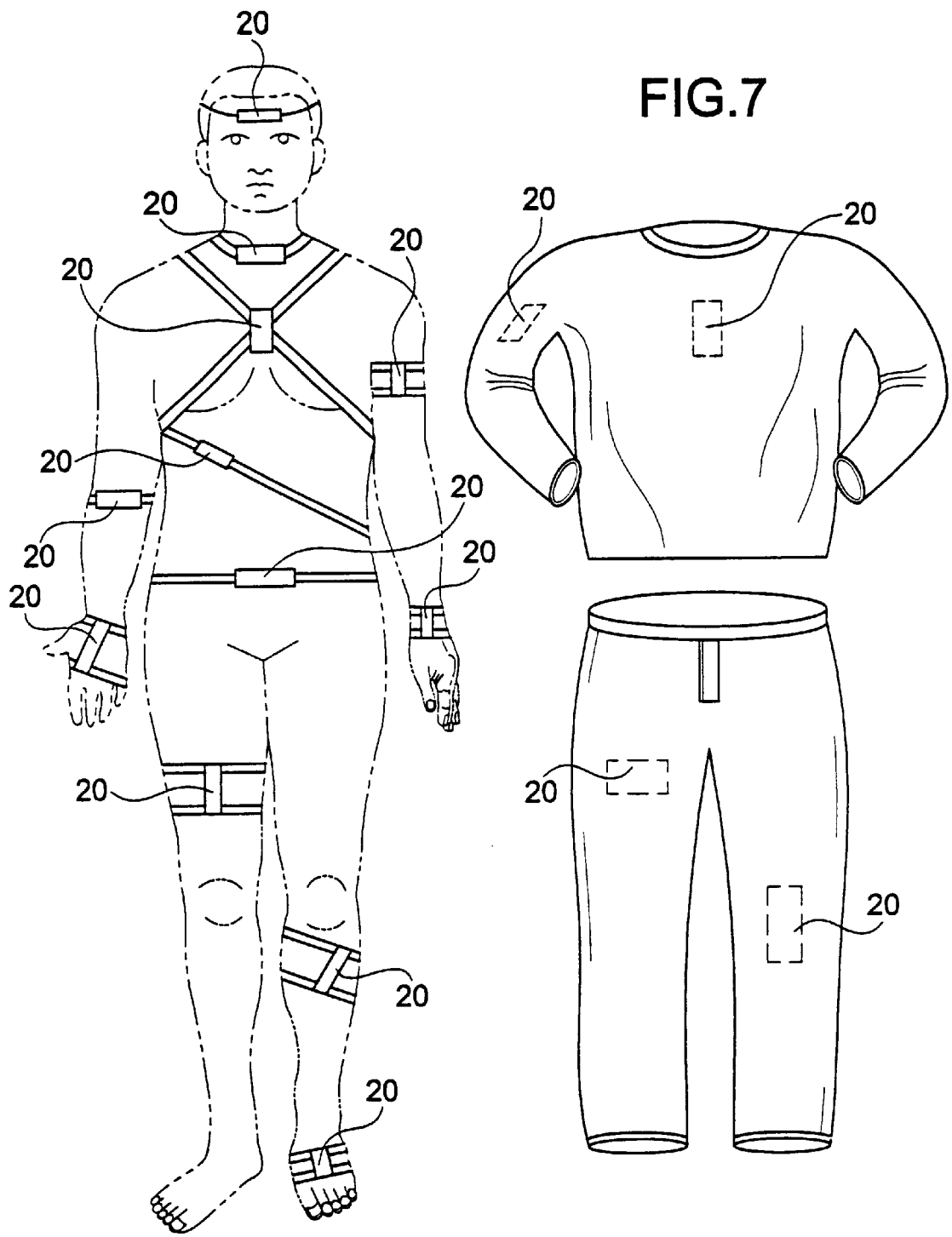
FIG. 6 shows alternative locations of the bioenergy channelizer unit on an organism such as the human body.
FIG. 7 shows one embodiment of the present invention where the bioenergy channelizer unit of the invention is applied to an article of apparel such as a shirt.
FIG. 8 shows one embodiment of the present invention where the bioenergy channelizer unit is applied to an article of apparel such as pants.

FIG. 6 provides alternate embodiments of the present invention where bioenergy channelizer units 20 are employed on reflex points at various parts of a living organism such as the human body, the units crossing that cross meridians as well as running parallel with meridians in the human body. The bioenergy channelizer unit 20 can be placed parallel to meridians in addition to at angles relative to meridians so that numerous meridians are crossed by the bioenergy channelizer unit 20 so that energy flows between or across respective meridians and/or between reflex points or areas. FIG. 7 shows bioenergy channelizer units 20 attached to an article of apparel such as a shirt.

In FIG. 8, a bioenergy channelizer unit is attached to another article of apparel such as pants. As stated above, the bioenergy channelizer unit is not limited for use with the human body and can be employed with other living organisms such as animals, plants and other life forms.

Figure 9:
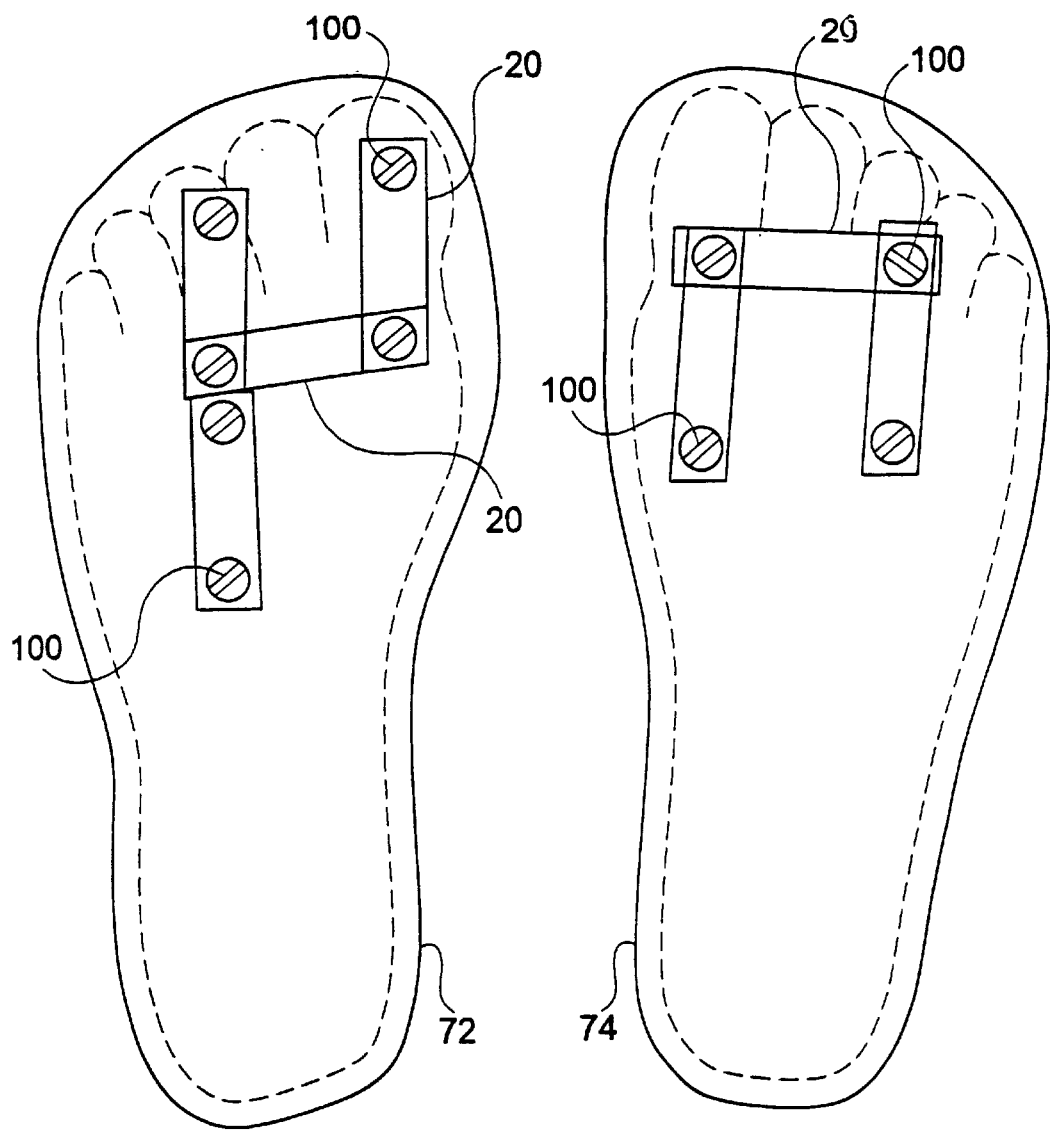
FIG. 9 shows one embodiment of the present invention where bioenergy channelizer units of the invention are applied to an article of apparel such as a footwear sole, the view being of left and right feet disposed behind the soles shown.
Figure 13:
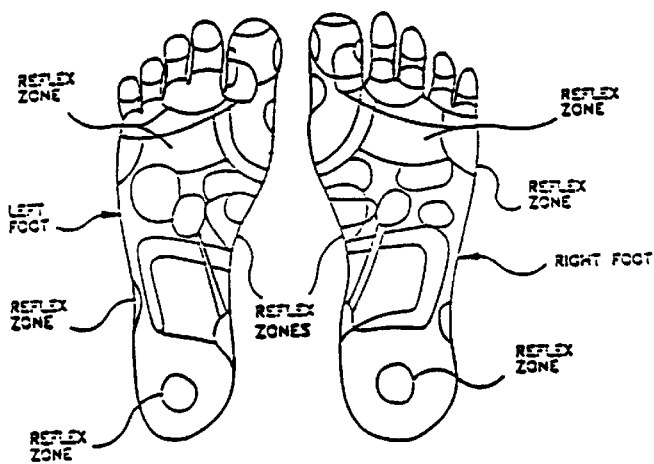
FIG. 13 shows background art of the locations of reflex points on the feet of an organism such as the human body.
Figure 14:
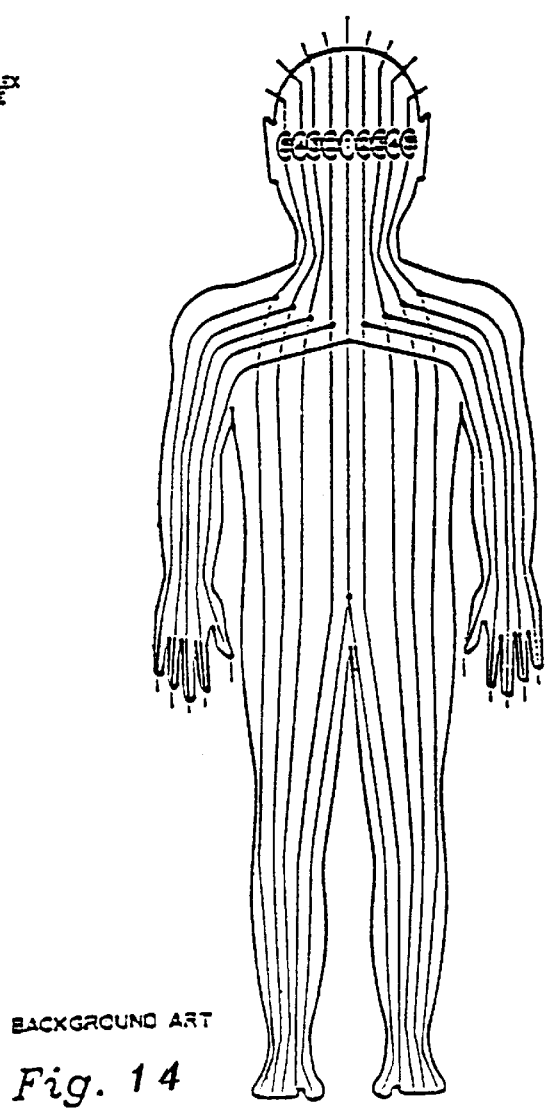
FIG. 14 shows background art on meridians or energy channels which are present in an organism such as the human body.
Figure 15A:
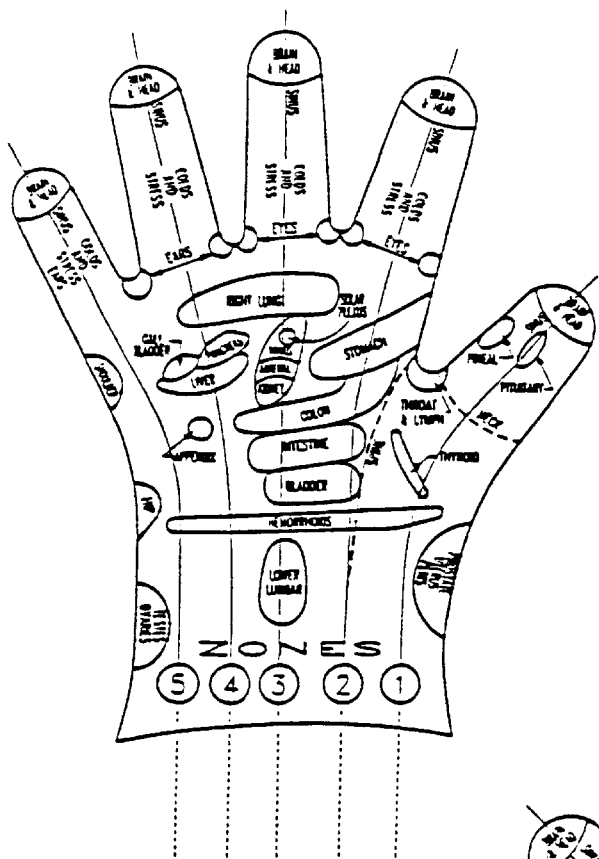
FIGS. 15A and 15B show background art of reflexology points on limbs of an organism such as the hands of a human body.
Figure 15B:
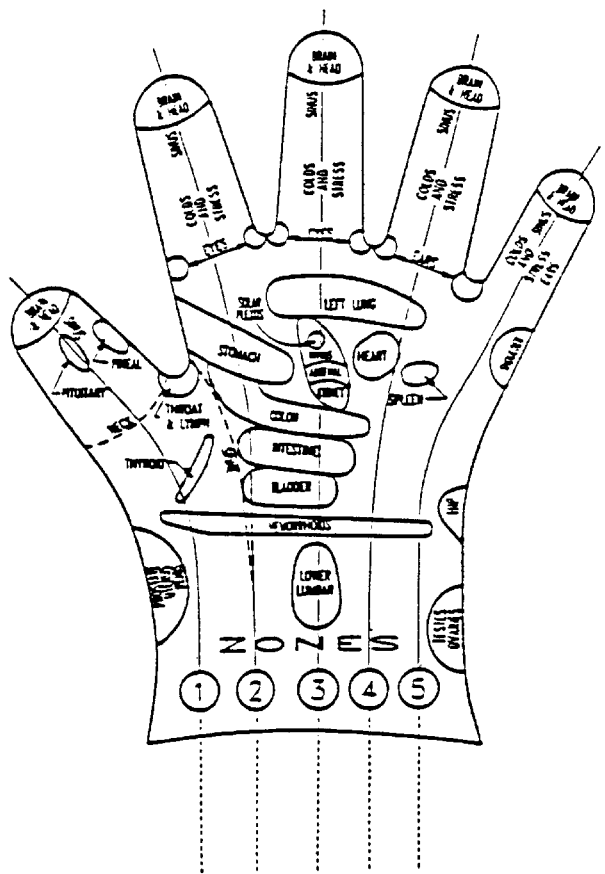

In FIG. 9, bioenergy channelizer units 20 which are shown in greater detail is provided in an article of apparel such as a foot sole as mentioned previously. The bioenergy channelizer units 20 extend between reflex points 100 in a fashion parallel with meridians or at angles with respect to meridians. The examples of reflex points and units 20 usage in FIG. 9 is merely illustrative and in no way limits the reflex points acted upon or the number of units used. As seen in FIG. 9, a first sole 72 and a second sole 74 include bioenergy channelizer units 20 which overlay reflex points 100. The view is through the bottom of the soles toward the feet on the opposite side thereof. By known manufacturing processes, the units are disposed within the foot soles, the second covering layer 42 either attached to or incorporated with the lower sole so as to face toward the lower sole surface away from the foot while the first covering layer 34 is adjacent to or forms a part of the upper sole surface which is adjacent to the foot. Preferably, the first covering layer portion beneath which lie the conductive elements extends flush with the surface of the upper sole surface, or more preferably, extends upwardly above the upper sole surface, such relationship being similarly available in any and all overlaying mechanisms.

In FIG. 10, a bioenergy channelizer unit 20 is fastened to a limb of an organism by a hand overlaying mechanism such as a glove 76. The bioenergy channelizer unit 20 is preferably attached within an inner surface of the glove 76 so that it is not perceptible by an observer.

In FIG. 11, bioenergy channelizer units 20 are disposed at multiple locations within a head overlaying mechanism such as a helmet 78. The head overlaying mechanism is not limited to the helmet 78 and can include further head overlaying mechanism such as hats, baseball caps or other like head overlaying mechanisms.

The bioenergy channelizer unit 20 provides a method for promoting energy flow in an organism 1. The method provides a plurality of conductive elements 22, 24, 26, 28, and 30 and placing the conductive elements on a first dielectric material layer 32 in a predetermined spatial relationship. Next, the method requires overlaying the dielectric material 32 with the conductive elements 22, 24, 26, 28, and 30 across predetermined regions of the organism. Once attached to the organism, channelizing energy with the conductive elements 22, 24, 26, 28, and 30 from a first reflex point in the vicinity of a first meridian of the organism occurs.

The received or channelized energy is then transmitted by the conductive elements 22, 24, 26, 28, and 30 to a second reflex point in the vicinity of at least one of the first meridian and a second meridian in the organism, whereby healthy flow of energy throughout the organism is substantially increased.

The method further includes a step of forming conductive material into a plurality of predetermined geometrical shapes and adhering the geometric conductive elements 22, 24, 26, and 28 to the first dielectric material layer 32.

The method further includes forming a plurality of apertures in a dielectric material or first covering layer 34 to increase the channelizing of energy from the organism. The method also includes steps of adhering the conductive elements 22, 24, 26, 28, and 30 to a second dielectric material 40, adhering the first dielectric material layer 32 to a first dielectric material covering layer 34, and adhering the second dielectric material 40 to a second dielectric material covering layer 42. The method further includes the step of fastening the dielectric material 32 having the conductive elements 22, 24, 26, 28, and 30, to an overlaying mechanism such as an article of apparel. As noted above, overlaying mechanisms include, but are not limited to, fabric materials which are expandable, adhesives, rubber materials, leather, Altacara, the afore-mentioned Silon, yarns, strings, adhesive tapes, or other like fastening structures which can attach to a living organism.

The present invention promotes energy flow in an organism which does not require extensive mechanical manipulation of reflex points or meridian termini of an organism. The invention provides a bioenergy channelizer unit which promotes healthy energy flow in an organism which can be worn on various parts of an organism to receive and transmit energy to and from the organism. The present invention is worn by an organism on, or in the vicinity of, reflex points or meridian termini in order to promote healthy energy flow through specific organs, glands, or systems within the organism. The bioenergy channelizer unit promotes healthy energy flow without the organism readily perceiving the presence of the bioenergy channelizer unit. The bioenergy channelizer unit promotes healthy energy flow throughout an organism by substantially reducing energy imbalances (deficient or excess energy) which exist along or in the vicinity of meridians in an organism. The bioenergy channelizer unit also promotes healthy flow of energy along or in the vicinity of energy channels or meridians in the organism and the balancing of energy within meridians and across meridians.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for promoting energy flow in an organism comprising the steps of:

overlaying and positioning an apparatus across at least one predetermined region of the organism, the region including at least two reflex points in the vicinity of one or more meridians of the organism, the apparatus including:

a dielectric material, and a plurality of conductive elements said plurality of conductive elements being disposed on said dielectric material in a predetermined spatial relationship, and said plurality of conductive elements including a first set and a second set of conductive elements, said first set of conductive elements having a first predetermined geometrical shape, and said second set of conductive elements having a second predetermined geometrical shape, such that at least one of said first set of conductive elements is positioned in the vicinity of one of the at least two reflex points;

channelizing energy with said first set of conductive elements from one of the at least two reflex points;

transmitting the channelized energy via said at least one of said second set of conductive elements received from the first reflex point toward another one of the at least two reflex points, whereby healthy flow of energy within the organism is substantially increased.

2. The method of claim 1, wherein said plurality of conductive elements is adhered to said dielectric material.

3. The method of claim 1, wherein said apparatus further includes a first dielectric material covering layer, said dielectric material is a first dielectric material, said plurality of conductive elements adhere to said first dielectric material, and said first dielectric material adheres to said first dielectric material covering layer.

4. The method according to claim 3, wherein said apparatus further includes a second dielectric material, said second dielectric material overlaying at least one of said plurality of conductive elements.

5. The method of claim 4, wherein said apparatus further includes a second dielectric material covering layer, said second dielectric material covering layer being adhered to said second dielectric material.

6. The method of claim 5, wherein said second dielectric material covering layer has a plurality of apertures therein, whereby energy flow between the organism and the conductive elements is substantially enhanced.

7. The method of claim 1, wherein said apparatus further includes an organism overlaying mechanism.

8. The method of claim 7, wherein the organism overlaying mechanism is a footwear sole.

9. The method of claim 7, wherein the organism overlaying mechanism is a foot overlaying mechanism.

10. The method of claim 7, wherein the organism overlaying mechanism is a hand overlaying mechanism.

11. The method of claim 7, wherein the organism overlaying mechanism is a head overlaying mechanism.

12. The method of claim 7, wherein the organism overlaying mechanism is a torso overlaying mechanism.

13. The method of claim 7, wherein the organism overlaying mechanism is an arm overlaying mechanism.

14. The method of claim 7, wherein the organism overlaying mechanism is a leg overlaying mechanism.

15. The method of claim 7, wherein the organism overlaying mechanism is a wrist overlaying mechanism.

16. The method of claim 1, wherein at least one of said plurality of conductive elements is formed from at least one of silver, gold, and copper.

17. The method of claim 16, wherein said at least one of said plurality of conductive elements is formed from silver.

18. The method of claim 1, wherein said first set of conductive elements includes triangularly shaped elements, and said second set of conductive elements includes quadrangularly shaped elements.

19. The method of claim 18, wherein said quadrangularly shaped elements are interposed between said triangularly shaped elements.

20. An apparatus for promoting energy flow in an organism comprising:

a dielectric material;

a plurality of conductive elements, said plurality of conductive elements being disposed on said dielectric material in a predetermined spatial relationship; and said plurality of conductive elements including a first set and a second set of conductive elements, said first set of conductive elements having a first predetermined geometrical shape, and said second set of conductive elements having a second predetermined geometrical shape; and means for overlaying and positioning said dielectric material with said conductive elements thereon across a predetermined region of the organism, the region including at least two reflex points in the vicinity of one or more meridians of the organism, such that at least one of said first set of conductive elements is positioned in the vicinity of one of the at least two reflex points for channelizing energy from one of the at least two reflex points and transmitting the energy received therefrom via one of said second set of conductive elements to another of the at least two reflex points in the vicinity of at least one of the one or more meridians, whereby healthy flow of energy within the organism is substantially increased.

21. The apparatus of claim 20, wherein said first set of conductive elements includes triangularly shaped elements, and said second set of conductive elements includes quadrangularly shaped elements.

22. The apparatus of claim 21, wherein said quadrangularly shaped elements are interposed between said triangularly shaped elements.

23. The apparatus of claim 20, wherein said dielectric material is an adhesive.

24. The apparatus of claim 20, wherein said dielectric material is a first dielectic material, and the apparatus further includes a second dielectric material and a first and a second dielectric covering layer, at least one of said plurality of conductive elements being disposed between said first and said second dielectric materials.

25. The apparatus of claim 24, wherein at least a portion of said first and said second dielectric materials are disposed between said first and said second dielectric material covering layers.

26. The apparatus of claim 25, wherein said first dielectric material covering layer includes a plurality of apertures, whereby energy flow between the organism and the conductive elements is substantially enhanced.

27. The apparatus of claim 20, wherein said overlaying means includes an article of apparel.

28. The apparatus of claim 20, wherein said overlaying means includes a footwear sole.

29. The apparatus of claim 20, wherein said overlaying means includes a foot overlaying mechanism.

30. The apparatus of claim 20, wherein said overlaying means includes a hand overlaying mechanism.

31. The apparatus of claim 20, wherein said overlaying means includes a head overlaying mechanism.

32. The apparatus of claim 20, wherein said overlaying means includes a torso overlaying mechanism.

33. The apparatus of claim 20, wherein said overlaying means includes an arm overlaying mechanism.

34. The apparatus of claim 20, wherein said overlaying means includes a leg overlaying mechanism.

35. The apparatus of claim 20, wherein said overlaying means includes a wrist overlaying mechanism.

36. The apparatus of claim 20, wherein said overlaying means includes a neck overlaying mechanism.

37. The apparatus of claim 20, wherein at least one of said plurality of conductive elements is formed from at least one of silver, gold, and copper.

38. The apparatus of claim 37, wherein the at least one of said plurality of conductive elements is formed from silver.

39. The method of claim 20, wherein at least one of said plurality of conductive elements is formed from ceramic material.

40. The apparatus of claim 37, wherein the at least one of said plurality of conductive elements is formed from ceramic material.

* * * * *